(12) United States Patent  
Shimano et al.

(10) Patent No.: US 10,117,623 B2  
(45) Date of Patent: Nov. 6, 2018

(54) BIOMETRIC AUTHENTICATION DEVICE AND BIOMETRIC AUTHENTICATION METHOD

(71) Applicant: HITACHI INDUSTRY & CONTROL SOLUTIONS, LTD., Hitachi-shi, Ibaraki (JP)

(72) Inventors: Kazuki Shimano, Hitachi (JP); Yasuhiro Shimizu, Hitachi (JP)

(73) Assignee: Hitachi Industry & Control Solutions, Ltd., Ibaraki (JP)

(*) Notice: Subject to any disclaimer, the term of this patent is extended or adjusted under 35 U.S.C. 154(b) by 247 days.

(21) Appl. No.: 15/036,957

(22) PCT Filed: Sep. 8, 2014

(86) PCT No.: PCT/JP2014/073604  
§ 371 (c)(1),  
(2) Date: May 16, 2016

(87) PCT Pub. No.: WO2015/114872  
PCT Pub. Date: Aug. 6, 2015

(65) Prior Publication Data  
US 2016/0256079 A1  Sep. 8, 2016

(30) Foreign Application Priority Data

Jan. 31, 2014 (JP) ................. 2014-016339

(51) Int. Cl.  
*A61B 5/00* (2006.01)  
*G06F 21/32* (2013.01)  
(Continued)

(52) U.S. Cl.  
CPC .......... *A61B 5/7271* (2013.01); *A61B 5/0059* (2013.01); *A61B 5/0082* (2013.01);  
(Continued)

(58) Field of Classification Search  
CPC ... A61B 5/0059; A61B 5/0082; A61B 5/1171; A61B 5/489; A61B 5/6826; A61B 5/72; A61B 5/7246; A61B 5/7271  
(Continued)

(56) References Cited

U.S. PATENT DOCUMENTS 8,229,178 B2 * 7/2012 Zhang ................ G06K 9/00067  
  348/77  
2001/0018557 A1 * 8/2001 Lynn .................. A61B 5/14551  
  600/324  
(Continued)

FOREIGN PATENT DOCUMENTS

JP  2008-079629 A  4/2008

OTHER PUBLICATIONS

International Search Report of PCT/JP2014/073604 dated Nov. 25, 2014.

*Primary Examiner* — Christopher A Flory  
(74) *Attorney, Agent, or Firm* — Mattingly & Malur, PC

(57) ABSTRACT

A biometric authentication device collates pre-registered biometric data for authentication with biometric data acquired during authentication. An imaging section images biometric data acquired by penetration through the finger by near-infrared light from a near-infrared light irradiating section. A control section acquires the biometric data acquired by the imaging section. A visible light irradiating section irradiates a finger inserting section where the finger is inserted with visible light. The visible light irradiating section starts irradiation of the visible light before the imaging section acquires the biometric data. The control section sets irradiation luminosity from the visible light irradiating section to be lower in a case where luminosity of an imaging screen of the biometric data acquired by the imaging section is higher than luminosity appropriate for authentication, and collates the biometric data in the case (Continued)

where the irradiation luminosity is set to be lower with the pre-registered biometric data for authentication.

8 Claims, 4 Drawing Sheets

(51) Int. Cl.
*G06K 9/00* (2006.01)
*A61B 5/1171* (2016.01)

(52) U.S. Cl.
CPC ............ *A61B 5/1171* (2016.02); *A61B 5/489* (2013.01); *A61B 5/6826* (2013.01); *G06F 21/32* (2013.01); *G06K 9/00013* (2013.01); *A61B 5/7246* (2013.01); *G06K 2009/00932* (2013.01)

(58) Field of Classification Search
USPC .......................................... 600/476; 607/476
See application file for complete search history.

(56) References Cited

U.S. PATENT DOCUMENTS

| | | | | |
|---|---|---|---|---|
| 2002/0173707 A1* | 11/2002 | Lynn | ................... | A61B 5/14551 600/323 |
| 2003/0179910 A1* | 9/2003 | Wong | ................ | G06K 9/00067 382/115 |
| 2005/0180620 A1* | 8/2005 | Takiguchi | .......... | G06K 9/00013 382/128 |
| 2007/0019845 A1* | 1/2007 | Kato | .................. | G06K 9/00013 382/126 |
| 2007/0116330 A1* | 5/2007 | Takiguchi | .......... | G06K 9/00013 382/115 |
| 2007/0217660 A1* | 9/2007 | Komura | ............. | G06K 9/00885 382/115 |
| 2008/0063244 A1* | 3/2008 | Tanaka | ............... | G06K 9/00033 382/115 |
| 2008/0075330 A1* | 3/2008 | Matsumura | .......... | A61B 5/1172 382/115 |
| 2008/0075332 A1 | 3/2008 | Fujisawa et al. | | |
| 2008/0118114 A1* | 5/2008 | Takiguchi | .......... | G06K 9/00013 382/124 |
| 2008/0298642 A1* | 12/2008 | Meenen | ................... | G06K 9/00 382/115 |
| 2008/0310690 A1* | 12/2008 | Higuchi | ............. | G06K 9/00046 382/124 |
| 2009/0074263 A1* | 3/2009 | Higuchi | ................ | A61B 5/1172 382/126 |
| 2009/0124376 A1* | 5/2009 | Kelly | .................. | G07F 17/3206 463/29 |
| 2009/0174526 A1* | 7/2009 | Howard | ............. | G06K 9/00006 340/5.52 |
| 2010/0045788 A1* | 2/2010 | Zhang | ................ | G06K 9/00067 348/77 |
| 2010/0198078 A1* | 8/2010 | Abe | ....................... | A61B 5/117 600/473 |
| 2010/0208948 A1* | 8/2010 | Abe | ..................... | A61B 5/0059 382/115 |
| 2010/0215223 A1* | 8/2010 | Abe | ..................... | A61B 5/0059 382/115 |
| 2010/0226545 A1* | 9/2010 | Abe | ..................... | A61B 5/0059 382/115 |
| 2010/0239129 A1* | 9/2010 | Abe | ..................... | A61B 5/0059 382/115 |
| 2011/0025835 A1* | 2/2011 | Higuchi | ............... | A61B 5/1172 348/77 |
| 2011/0038511 A1* | 2/2011 | Takiguchi | .......... | G06K 9/00013 382/115 |
| 2012/0148143 A1* | 6/2012 | Takiguchi | .......... | G06K 9/00013 382/134 |
| 2012/0162403 A1* | 6/2012 | Bae | ........................ | H04N 7/183 348/77 |
| 2012/0263357 A1* | 10/2012 | Xu | ..................... | G06K 9/00013 382/128 |
| 2013/0160141 A1* | 6/2013 | Tseng | ................... | G06F 21/6245 726/28 |
| 2013/0208359 A1* | 8/2013 | Matsuno | ................ | G02B 5/284 359/578 |
| 2013/0243264 A1* | 9/2013 | Aoki | .................. | G06K 9/00013 382/115 |
| 2014/0016830 A1* | 1/2014 | Wang | .................. | G06K 9/00885 382/115 |
| 2014/0019489 A1* | 1/2014 | Wang | ................. | G06F 17/30961 707/797 |
| 2014/0025607 A1* | 1/2014 | Wang | ................. | G06F 17/30247 706/12 |
| 2014/0086459 A1* | 3/2014 | Pan | ..................... | G06K 9/00006 382/124 |
| 2014/0119617 A1* | 5/2014 | Bertin | ................ | G06K 9/00892 382/116 |
| 2014/0139318 A1* | 5/2014 | Malpani | ................... | G06F 21/32 340/5.82 |
| 2014/0183269 A1* | 7/2014 | Glaser | ...................... | G06F 21/32 235/492 |
| 2014/0194748 A1* | 7/2014 | Yamamoto | ........... | A61B 5/0059 600/473 |
| 2014/0282945 A1* | 9/2014 | Smith | ...................... | G06F 21/32 726/6 |
| 2014/0301610 A1* | 10/2014 | Takiguchi | .......... | G06K 9/00013 382/115 |
| 2015/0036893 A1* | 2/2015 | Shinzaki | ............... | H04L 9/3231 382/115 |
| 2015/0046711 A1* | 2/2015 | Slaby | ........................ | H04L 63/08 713/170 |
| 2015/0046996 A1* | 2/2015 | Slaby | ........................ | H04L 63/08 726/7 |
| 2015/0121514 A1* | 4/2015 | Park | ........................ | G06F 21/34 726/19 |
| 2015/0261991 A1* | 9/2015 | Takiguchi | .......... | G06K 9/00013 382/124 |
| 2015/0310252 A1* | 10/2015 | Aoki | .................. | G06K 9/00033 382/115 |
| 2015/0356285 A1* | 12/2015 | Glaser | ...................... | G06F 21/32 726/7 |
| 2016/0006732 A1* | 1/2016 | Smith | ...................... | G06F 21/32 726/6 |
| 2016/0011290 A1* | 1/2016 | Iannello | ................ | A61B 5/055 600/309 |
| 2016/0104028 A1* | 4/2016 | Pan | ..................... | G06K 9/00006 382/124 |
| 2016/0167672 A1* | 6/2016 | Krueger | ................ | A61M 21/00 340/576 |
| 2016/0171201 A1* | 6/2016 | Schroder | ............... | H04B 5/0031 726/20 |
| 2016/0292404 A1* | 10/2016 | Tseng | ................... | G06F 21/6245 |
| 2017/0053253 A1* | 2/2017 | Glaser | ...................... | G06F 21/32 |
| 2017/0244684 A1* | 8/2017 | Smith | ...................... | H04L 63/06 |

\* cited by examiner

BIOMETRIC AUTHENTICATION DEVICE AND BIOMETRIC AUTHENTICATION METHOD

TECHNICAL FIELD

The present invention relates to a biometric authentication device, and particularly relates to a device for authenticating an individual using a vein pattern acquired by irradiating a finger with near-infrared rays, and a program of the same.

BACKGROUND ART

Amid a recently increasing interest in a security technique for personal possessions and information, with an aim to enhance security and convenience at, for example, office buildings in particular, attention has been drawn to a biometric authentication technique including a fingerprint, iris, vein, voice, and the like as a personal authentication technique with superior confidentiality and less risk of fraudulent use due to theft or loss as well as an authentication medium such as a non-contact card. Above all, finger vein authentication allowing authentication only by irradiating a finger with near-infrared rays causes less psychological resistance, uses internal information of a living body, and thus, is superior in resistance to forgery.

As a related art in the present technical field, there is JP 2008-79629 A (PTL 1). Described in this publication is a clause stating, "a finger placing section that supports and positions a finger to be authenticated in contact with a pad side part thereof is formed in a case, which has a configuration where parts corresponding to upper and bottom sides and left and right sides of the finger to be authenticated are closed, parts corresponding to front and back sides thereof are open, and an imaging range of an imaging means such as an imaging element is formed inside the parts corresponding to the left and right sides thereof" (see ABSTRACT).

CITATION LIST

Patent Literature

PTL 1: JP 2008-79629 A

SUMMARY OF INVENTION

Technical Problem

In the above PTL 1, a configuration of a housing of a biometric authentication device is described. However, a near-infrared light source section is included so as to cover an upper portion of an imaging section (back side of a finger), and a case is formed such that parts corresponding to upper and bottom sides and left and right sides of the finger are closed, thereby shielding external light. Thus, the finger is inserted into a closed space of the authentication device. Therefore, there is a problem of a sense of insecurity in the finger insertion.

Thus, by irradiating a finger inserting section with visible light (for example, LED lighting), a user can insert a finger into the authentication device with a sense of security during finger insertion. However, this irradiation of visible light may change brightness of an image of a vein pattern used in carrying out authentication and deteriorate authentication accuracy of the biometric authentication device.

Therefore, an object of the present invention is to provide a biometric authentication device that allows, in a biometric authentication device including a near-infrared light source section so as to cover an upper portion of an imaging section, a user to insert a finger with a sense of security during finger insertion into the authentication device as well as carry out authentication with a sense of security by maintaining an inside of the authentication device visually recognizable with authentication accuracy ensured.

Solution to Problem

Provided to solve the problem is a biometric authentication device for carrying out biometric authentication using biometric information by collating pre-registered biometric data for authentication with biometric data acquired during authentication, including: a near-infrared light irradiating section that irradiates a finger with near-infrared light; an imaging section that images biometric data acquired by penetration through the finger by the near-infrared light emitted from the near-infrared light irradiating section; a control section that acquires the biometric data acquired by the imaging section; and a visible light irradiating section that irradiates a finger inserting section where the finger is inserted with visible light, wherein the visible light irradiating section starts irradiation of the visible light before the imaging section acquires the biometric data, and the control section sets irradiation luminosity from the visible light irradiating section to be lower in a case where luminosity of an imaging screen of the biometric data acquired by the imaging section is higher than luminosity appropriate for authentication, and collates the biometric data in the case where the irradiation luminosity is set to be lower with the pre-registered biometric data for authentication.

Advantageous Effects of Invention

According to the present invention, in a biometric authentication device including a near-infrared light source section so as to cover an upper portion of an imaging section, a user can insert a finger with a sense of security during finger insertion into the authentication device and carry out authentication with a sense of security by maintaining an inside of the authentication device visually recognizable with authentication accuracy ensured.

DESCRIPTION OF EMBODIMENTS

Next, an embodiment of the present invention (hereinafter referred to as the "present embodiment") will be described in detail with reference to the drawings as necessary.

These are each an example of the present invention and do not limit configurations and functions thereof.

Particularly in the present example, finger vein authentication will be described, but the present example can be applied to a device for imaging and authenticating a vein pattern generated by irradiating and penetrating a finger with near-infrared light such as vein authentication of a palm. The present example can be applied not only to the finger vein authentication device but also to a fingerprint authentication device, and to a device configured to be incapable of directly and visually recognizing a site to be authenticated of a living body.

Figure 1:
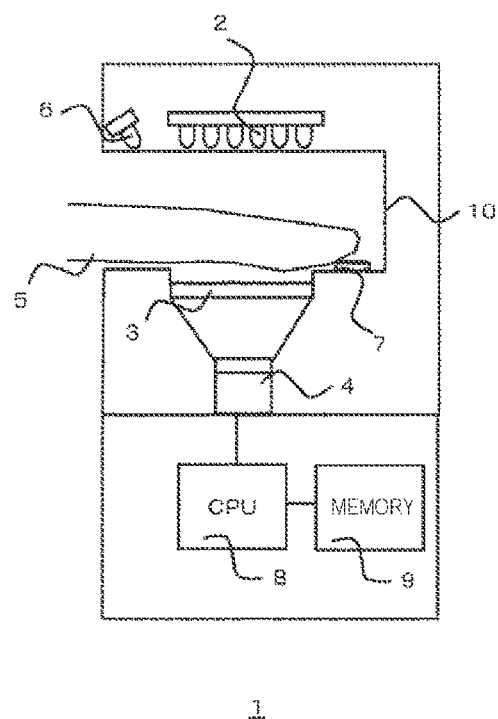
FIG. 1 is an exemplary configuration of an input interface of a finger vein authentication device according to an embodiment of the present invention.

FIG. 1 is a sectional view of the finger vein authentication device for realizing the present invention. An authentication device 1 may be a device for carrying out authentication by inserting a finger into the device such as the finger vein authentication device and the fingerprint authentication device, but in the following example, the authentication device 1 applying the finger vein authentication will be described as an example.

The authentication device 1 includes a near-infrared light irradiating section 2, a photographing window 3, a camera 4, a visible light irradiating section 6, an authentication switch 7, a CPU 8, and a memory 9. The authentication device 1 has, for example, as illustrated in FIG. 1, an inserting section 10, into which a finger 5 is inserted, formed in a housing 1. The inserting section 10 is formed to be substantially U-shaped when viewed from a side surface of the finger 5.

The near-infrared light irradiating section 2 is provided on a back side of the finger in a case where the finger 5 is placed in the inserting section 10. When the finger 5 is irradiated with the near-infrared light from this near-infrared light irradiating section 2, the near-infrared light that has scattered inside the finger 5 is emitted outside a body from a pad side of the finger 5. At this time, hemoglobin in the blood is high in near-infrared ray absorptivity and absorbs more near-infrared light than surrounding tissues. Therefore, the near-infrared light is emitted with veins distributed under the skin of the pad side of the finger 5 in shadow.

Figure 2:
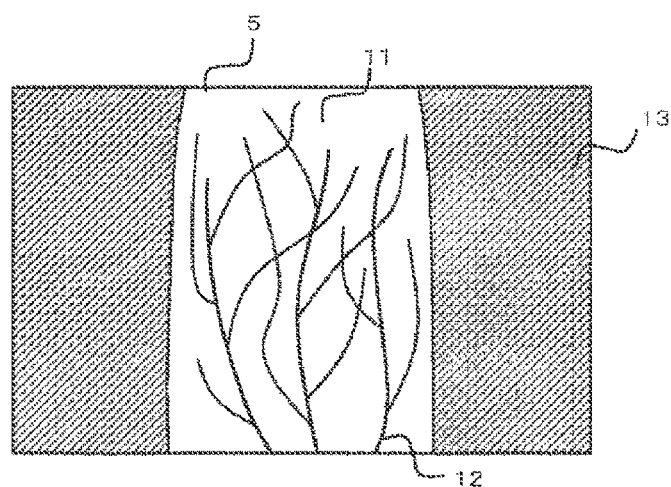
FIG. 2 is a diagram illustrating an exemplary finger vein pattern during normal authentication.

FIG. 2 is an example of the vein pattern of the finger 5 imaged by the authentication device in FIG. 1 above. An area 11 where the near-infrared light scatters inside the finger 5 and an amount of light thereof is large is shown in white, while a vein area 12 where the near-infrared light is absorbed in the hemoglobin in the blood and a periphery 13 of the finger 5 which is not irradiated with the near-infrared light have less amount of light thereof and thus are shown in black. As a result, the vein pattern formed by an outline of the finger 5 and the vein area 12 can be recognized.

Referring back to FIG. 1, the emitted near-infrared light penetrates an imaging window 3, images by the camera 4, and acquires vein patterns necessary for authentication. The photographing window 3 may be provided with an unillustrated filter that transmits only the near-infrared light or other filters, lenses, or the like for clearly imaging the vein patterns. In addition, it is possible to further miniaturize the finger vein authentication device 1 by reflecting the near-infrared light for imaging via, for example, a mirror (not illustrated) between the imaging window 3 and the camera 4.

As for the near-infrared light irradiating section 2, the finger 5 may be irradiated from the side surface, the pad side, or the front thereof, and not from the back side thereof. In FIG. 1, a plurality of light sources of the near-infrared light irradiating section 2 is illustrated in one row along an insertion direction of the finger 5, but one light source may be acceptable. The light source may also be arranged in a vertical direction to the insertion direction of the finger 5, or arranged in a sheet form with respect to the back side of the finger 5. The near-infrared light to be emitted from the light source may be diffused using, for example, a lens (not illustrated), or may be moved to a position of the finger 5. Furthermore, luminance of a plurality of light sources may be all equivalent or different, and may be a fixed value or variable value. By adopting such a configuration, it is possible to uniformly image the vein patterns of the whole finger 5 by increasing the amount of light at sites hard to transmit the near-infrared light and decreasing the amount of light at sites easy to transmit the near-infrared light.

A timing for irradiation of the near-infrared light by the light source of the near-infrared light irradiating section 2 may be constant, or only in a case where the insertion of the finger 5 is imaged and recognized by the authentication switch 7 and various types of sensors (not illustrated) installed at a tip or base of a finger, and the camera 4.

Next, the vein patterns imaged by irradiation of the near-infrared light by the near-infrared light irradiating section 2 are converted into an electrical signal and identified at the CPU 8 via unillustrated interface IC. After once being housed in the memory 9 connected to the CPU 8, the vein patterns are collated with those registered in advance. The pre-registered vein patterns are housed in a storage medium such as a random access memory (RAM) mounted in the finger vein authentication device 1 together with IDs and numbers for identifying an individual. Here, in the above collation processing, collation with pre-registered vein data is carried out in the finger vein authentication device 1, but is not limited to the processing in the present finger vein authentication device 1. The registered data may be, for example, stored and collated at an unillustrated control panel, PC, server, or the like connected to the present finger vein authentication device 1 for returning only results of the authentication to the finger vein authentication device 1 from the control panel, PC, or server.

As for acquisition of the vein patterns, in a case where the vein patterns are imaged by the camera 4, they may be acquired by being constantly imaged by the camera 4 for determining that the finger 5 is completely inserted. In addition, the vein patterns may be acquired by starting being imaged by the camera 4 in a case where the finger 5 is recognized to be completely inserted by the authentication switch 7 or the unillustrated various types of sensors installed at the tip of the finger.

In the collation processing, a correlation value between two sheets of data to be compared with each other is calculated for determining whether or not the value corresponds with the registered vein data in accordance with the value. Based on this result, an individual is authenticated, and the results of the authentication are displayed by a display means 15 such as an LED illustrated in FIG. 3 to be described later, and reported to the user. The means for displaying the results of the authentication is not limited to, for example, unillustrated LEDs and images, and may be any means that reports the results of the authentication to the user such as a buzzer and voice output.

Figure 3:
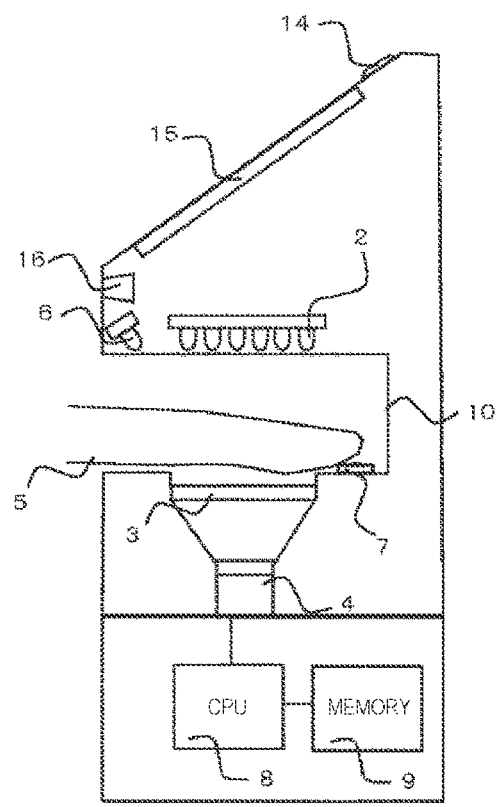
FIG. 3 is an exemplary configuration of an input interface of a finger vein authentication device according to an embodiment of the present invention (in a case where an input section such as liquid crystal with a touch panel is provided).

In the present example, in a case where the collation processing described above is carried out, the visible light irradiating section 6 is included in order to reduce a sense of insecurity of the user and guide the insertion into the housing when the user inserts the finger 5 into the finger inserting section 10. Here, the visible light irradiating section 6 is assumed to be visible LED light, but may be, for example, a halogen lamp, and may be what illuminates an area where the finger is placed inside the finger vein authentication device 1, particularly in the finger inserting section 10. The visible light may be installed not only on an upper portion of the back side of the finger 5 in the finger inserting section 10 as illustrated in FIG. 1 or 3, but also on a side surface or lower portion of the finger inserting opening, or at the depth thereof as long as the visible light is not blocked by the finger 5 when the finger 5 is completely inserted and without influence on imaging by a camera 3. Operations of the visible light irradiating section 6 will be described in detail in FIGS. 4 and 5 to be described later.

FIG. 3 is a second embodiment of a finger vein authentication device 1 for realizing the present invention. Of numbers given in FIG. 3, the descriptions of those that overlap in FIG. 1 will be omitted. An upper section of a housing of the finger vein authentication device 1 is provided with a lighting switch 14, a liquid crystal 15 with a touch panel, and a human sensor 16.

Meanwhile, an authentication system of the finger vein authentication device 1 is roughly divided into the following two types. One is a 1:N authentication system that collates whether or not there are data corresponding with vein data acquired from a user from among vein patterns pre-registered in a memory 9 of the finger vein authentication device 1. The other is a 1:1 authentication system that identifies an individual by other authentication devices such as a card reader connected to the finger vein authentication device 1 or connected via an unillustrated control panel, and collates whether or not associated vein data of an individual correspond with the vein data acquired from a user.

Figure 4:
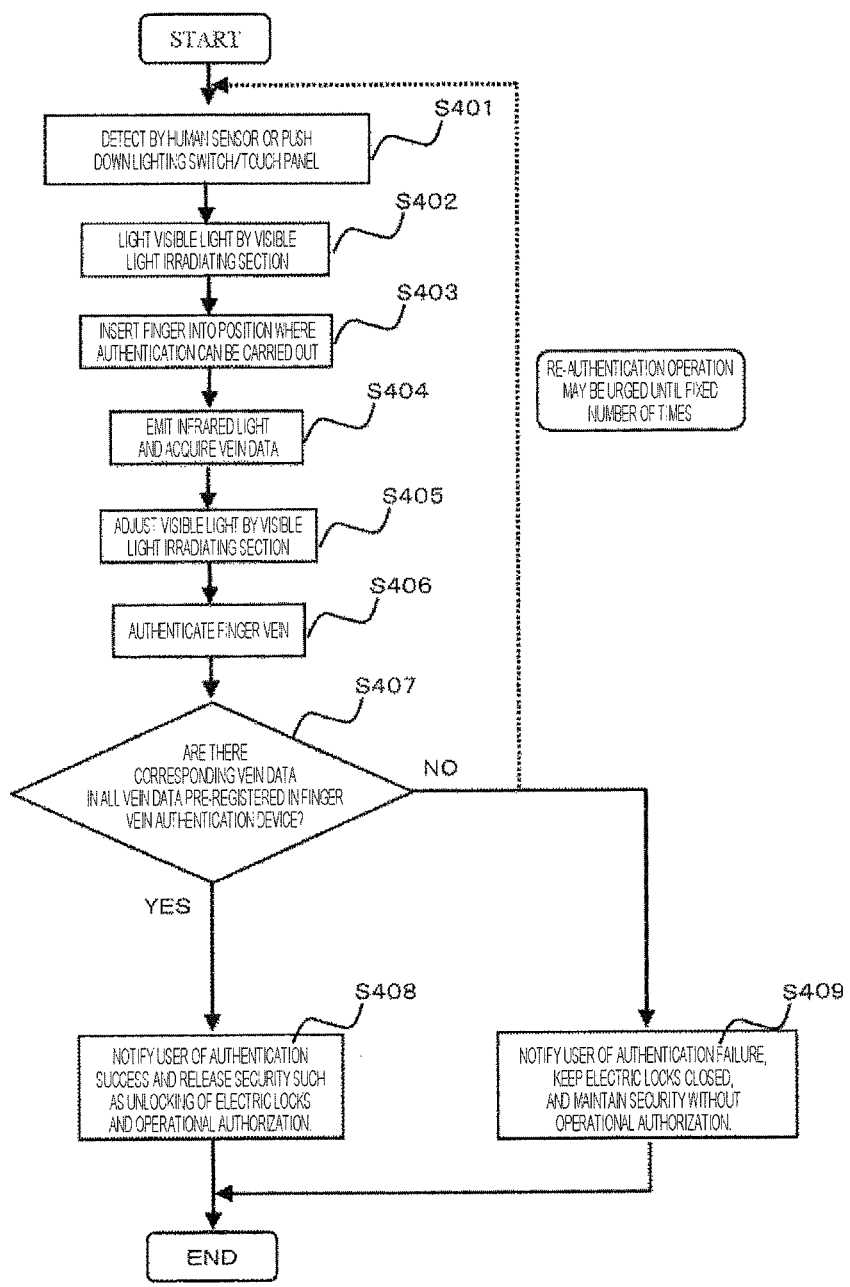
FIG. 4 is a flowchart illustrating a timing for turning on/off visible light when a 1:N authentication system is employed.
Figure 5:
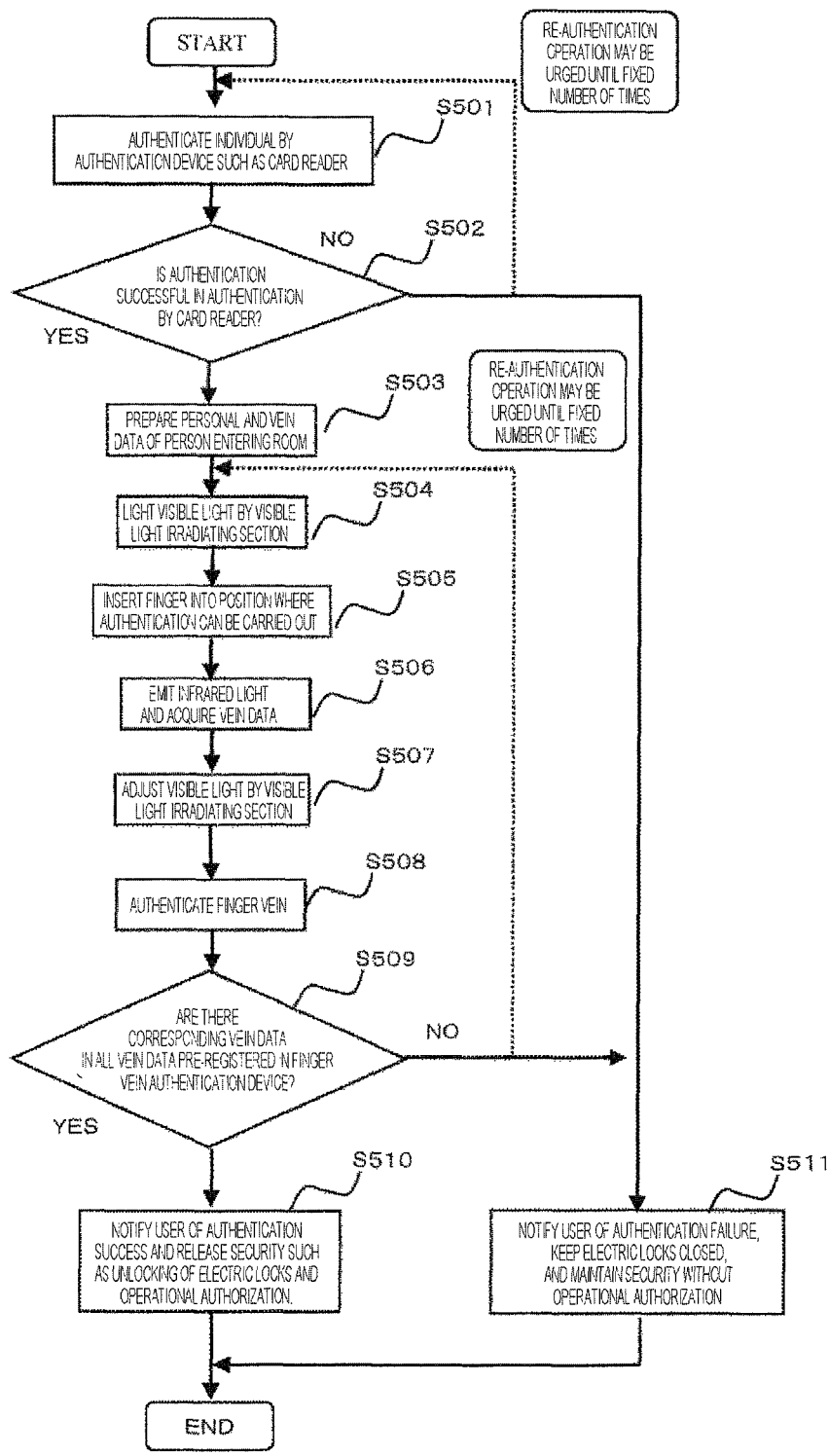
FIG. 5 is a flowchart illustrating a timing for turning on/off visible light when a 1:1 authentication system is employed.

FIG. 4 illustrates a flowchart in the present example in the 1:N authentication system. FIG. 5 illustrates a flowchart in the present example in the 1:1 authentication system.

Initially, a method for lighting a visible light irradiating section 6 in the 1:N authentication system will be described, based on a flow of FIG. 4, in an exemplary configuration of an input interface of a finger vein authentication device according to an embodiment of the present invention illustrated in FIG. 3 as an example.

First, when the user approaches the finger vein authentication device 1, the human sensor 16 detects the user. Here, a method for detecting the user is not only the human sensor 16. The user may be detected by the lighting switch 14 or pushing-down of, for example, a touch panel of the liquid crystal 15 with a touch panel for irradiation of visible light from the visible light irradiating section 5 (step 401).

In a case where the user is detected in step 401, a finger inserting section 10 inside the finger vein authentication device 1 is irradiated with the visible light from the visible light irradiating section 6 (step 402). This can illuminate the finger inserting section 10 for reducing a sense of insecurity of the user, and have the user recognize that finger vein authentication can be ready for prompting insertion of a finger 5.

The user confirms that the inside of the finger vein authentication device 1 is irradiated and illuminated with the visible light from the visible light irradiating section 6, and inserts the finger 5 into the finger inserting section 10 (step 403).

In a case where the finger 5 is inserted into the finger inserting section 10, the insertion of the finger 5 is recognized by an authentication switch 7 or various types of sensors (not illustrated) installed at a tip of the finger, or imaging by a camera 3. After the insertion of the finger 5 is recognized, near-infrared light is emitted from a near-infrared light irradiating section 2. The emitted near-infrared light enters inside the finger 5, and the near-infrared light that has scattered inside the finger 5 is emitted outside a body from a pad side of the finger 5. The emitted near-infrared light penetrates an imaging window 3, images by a camera 4, and acquires vein data (step 404).

The acquired vein data acquires luminosity of the vein data in a CPU 8. A memory 9 has luminosity appropriate for vein authentication as luminosity data, and the CPU 8 compares luminosity of the acquired vein data with the luminosity data. In a case where the luminosity of the acquired vein data is higher than the luminosity data, irradiation luminosity of the visible light is controlled to be lower such that the luminosity becomes appropriate for authentication. At this time, by controlling the irradiation luminosity to be lower without turning-off of the visible light, authentication processing is carried out while the finger 5 under authentication is irradiated with the visible light. Therefore, a cooped-up feeling of the user in finger insertion before and during the authentication is reduced, and the user can carry out authentication with a sense of security. On the other hand, in a case where the luminosity of the acquired vein data is lower than the luminosity data, the irradiation luminosity of the visible light is controlled to be maintained or lower. Adopting such a configuration can, as described above, reduce the user's cooped-up feeling in the finger insertion before and during the authentication and allow the user to carry out the authentication with a sense of security (405). At this time, a decrement in illumination luminosity in a case where the luminosity of an imaging screen of biometric data acquired by an imaging section is lower than the luminosity appropriate for authentication is set smaller than the decrement in illumination luminosity in a case where the luminosity of the imaging screen of the biometric data acquired by the imaging section is higher than the luminosity appropriate for authentication. This can provide the user with a sense of security during the authentication by preventing reduction in irradiating amount as much as possible in a case where an irradiating amount of the visible light is luminosity without influence on a vein pattern.

The visible light irradiating section 6 can change blinking patterns and colors in accordance with an authentication mode. It is also possible to notify the user by lighting the lighting switch 14 as well in accordance with the authentication mode.

Next, the finger vein patterns after the luminosity becomes appropriate for the finger vein authentication in step 405 are acquired for starting the finger vein authentication. Then, it is collated whether or not there are corresponding data from among the acquired vein data (step 406).

If there are data corresponding with the vein data acquired from the user (YES in step 407), illuminations and liquid crystal displays, buzzers, liquid crystal displays, and the like are used to notify the user that authentication is successful. If the present example is applied to an access management system, electric locks, automatic doors, and the like are unlocked, and security is released in other devices (step 607). Then, the authentication processing is finished, and the visible light irradiating section 6 is turned off.

On the other hand, if there are no data corresponding with the vein data acquired from the user (NO in step 406), illuminations and liquid crystal displays, buzzers, liquid crystal displays, and the like are used to notify the user that authentication is failed. If the present example is applied to an access management system, electric locks, automatic doors, and the like are kept closed, and security is maintained in other devices (step 408). Then, the authentication processing is finished, and the visible light irradiating section 6 is turned off.

Next, a lighting method in the 1:1 authentication system will be described in line with the flowchart illustrated in FIG. 5.

Before carrying out personal authentication in a finger vein authentication device 1, a user carries out authentication by other authentication devices such as a card reader connected to the finger vein authentication device 1 or connected via an unillustrated control panel (501).

If authentication by a card reader is successful (YES in step 502), a personal ID of the user is prepared and preparations for vein authentication based on vein data associated with the personal ID are carried out (step 503).

If authentication by a card reader is failed (NO in step 502), the user is notified, of the authentication failure using illuminations by a visible light irradiating section 6, a liquid crystal display 15, a buzzer, and the like, and security is maintained (step 510).

On the other hand, if the authentication by the card reader is successful, a finger inserting section 10 inside the finger vein authentication device 1 is irradiated with visible light by the visible light irradiating section 6 (step 504). Such a configuration enables the user to visually recognize what to authenticate by a biometric authentication device as a next authentication operation. Here, a means to notify the user of results of the authentication by the card reader may be turning on or off of a light in conjunction with the visible light from the visible light irradiating section 6 originally provided for illuminating the finger inserting section 10. The user may also be notified by changing blinking patterns, colors, or areas to be lighted in accordance with the authentication mode and the results of the authentication.

The user confirms that the finger inserting section 10 inside the finger vein authentication device 1 is irradiated and illuminated with the visible light from the visible light irradiating section 6 and inserts a finger 5 into the finger inserting section 10 (step 505). In a case where the finger is inserted into the finger inserting section 10, the insertion of the finger 5 is recognized by an authentication switch 7 or various types of sensors (not illustrated) installed at a tip of the finger, or imaging by a camera 3. After the insertion of the finger 5 is recognized, near-infrared light is emitted from a near-infrared light irradiating section 2. The emitted near-infrared light enters inside the finger 5, and the near-infrared light that has scattered inside the finger 5 is emitted outside a body from a pad side of the finger 5. The emitted near-infrared light penetrates an imaging window 3, images by a camera 4, and acquires vein data (step 506).

The acquired vein data acquires luminosity of the vein data in a CPU 8. A memory 9 has luminosity appropriate for vein authentication as luminosity data, and the CPU 8 compares luminosity of the acquired vein data with the luminosity data. In a case where the luminosity of the acquired vein data is higher than the luminosity data, irradiation luminosity of the visible light is controlled to be lower such that the luminosity becomes appropriate for authentication. At this time, by controlling the irradiation luminosity to be lower without turning-off of the visible light, authentication processing is carried out while the finger 5 under authentication is irradiated with the visible light. Therefore, a cooped-up feeling of the user in finger insertion before and during the authentication can be reduced. On the other hand, in a case where the luminosity of the acquired vein data is lower than the luminosity data, the irradiation luminosity of the visible light is controlled to be maintained or lower. Adopting such a configuration can, as described above, reduce the user's cooped-up feeling in the finger insertion before and during the authentication and allow the user to carry out the authentication with a sense of security (step 507). At this time, a decrement in illumination luminosity in a case where the luminosity of an imaging screen of biometric data acquired by an imaging section is lower than the luminosity appropriate for authentication is set smaller than the decrement in illumination luminosity in a case where the luminosity of the imaging screen of the biometric data acquired by the imaging section is higher than the luminosity appropriate for authentication. This can provide the user with a sense of security during the authentication by preventing reduction in irradiating amount as much as possible in a case where an irradiating amount of the visible light is luminosity without influence on a vein pattern.

The visible light irradiating section 6 can change blinking patterns and colors in accordance with an authentication mode. It is also possible to notify the user by lighting the lighting switch 14 as well in accordance with the authentication mode.

The finger vein patterns after the luminosity becomes appropriate for the finger vein authentication in step 507 are acquired for starting the finger vein authentication. That is, it is collated whether or not there are corresponding data from among the acquired vein data (step 508).

It is collated whether or not there are corresponding vein data acquired from the user from among the vein data pre-registered in the memory 9 in the finger vein authentication device 1 (step 509). If there are data corresponding with the vein data acquired from the user (YES in step 509), illuminations by the visible light irradiating section 6, liquid crystal displays, buzzers, and the like are used to notify the user that authentication is successful. If the present example is applied to an access management system, electric locks, automatic doors, and the like are unlocked, and security is released in other devices (step 510). If there are no data corresponding with the vein data acquired from the user (NO in step 509), illuminations by the visible light irradiating section 6, liquid crystal displays, buzzers, and the like are used to notify the user that authentication is failed. If the present example is applied to the access management system, electric locks, automatic doors, and the like are kept closed, and security is maintained in other devices (step 511).

In authentication flows in FIGS. 4 and 5, after the finger vein authentication is started, if the authentication of vein data acquired from the user is successful, or if a way the finger 5 is placed is determined as inappropriate, it is possible to return to steps 402 and 504 for irradiation of the visible light again from the visible light irradiating section 6 and notify the user of the failure in the authentication or replacement of the finger 5. In terms of a way the visible light is shined at that time, the user may be notified by not only turning on or off the light, but also changing blinking patterns, colors, or areas to be lighted. The user may also be notified of the results of the authentication and replacement of the finger not only by a message via the visible light but also by using illuminations, liquid crystal displays, buzzers, and the like.

The present invention can be applied not only to the finger vein authentication device but also to a fingerprint authentication device, and to a device configured to be incapable of directly and visually recognizing a site to be authenticated of a living body.

REFERENCE SIGNS LIST

1 authentication device
2 near-infrared light irradiating section 3 imaging window
4 camera
5 finger
6 visible light irradiating section
7 authentication switch
8 CPU
9 memory

The invention claimed is:

1. A biometric authentication device for carrying out biometric authentication using biometric information by collating pre-registered biometric data for authentication with biometric data acquired during authentication, the device comprising:
 a housing that defines a finger inserting section;
 a near-infrared light source configured to irradiate a finger in the finger inserting section with near-infrared light;
 a visible light source configured to irradiate the finger inserting section with visible light;
 a camera configured to capture a first image of the finger in the finger inserting section with the near-infrared light which penetrates through the finger while the visible light source irradiates the finger inserting section with the visible light;
 a memory configured to store the pre-registered biometric data and a predetermined luminosity; and
 a processor programmed by executable instructions to acquire biometric data from the first image,
 wherein the visible light source is configured to start irradiation of the visible light before the camera captures the image, and
 when a luminosity of the acquired biometric data from the first image is higher than the predetermined luminosity, the processor is further programmed by the executable instructions to:
 lower an irradiation luminosity from the visible light source
 cause the camera to capture a second image of the finger in the finger inserting section with the near-infrared light which penetrates through the finger while the visible light source irradiates the finger inserting section with the lowered visible light from the visible light source,
 acquire biometric data from the second image, and
 collate the acquired biometric data from the second image with the pre-registered biometric data for authentication.

2. The biometric authentication device according to claim 1,
 wherein, when the luminosity of the acquired biometric data from the first image is lower than the predetermined luminosity, the processor is further programmed by the executable instructions to:
 maintain the irradiation luminosity from the visible light source to be unchanged or lower the irradiation luminosity from the visible light source,
 cause the camera to capture a second image of the finger in the finger inserting section with the near-infrared light which penetrates through the finger while the visible light source irradiates the finger inserting section with the maintained or lowered visible light from the visible light source,
 acquire biometric data from the second image, and
 collate the acquired biometric data from the second image with the pre-registered biometric data for authentication.

3. The biometric authentication device according to claim 2,
 wherein an amount the illumination luminosity is lowered when the luminosity of the acquired biometric data from the first image is higher than the predetermined luminosity is smaller than an amount the illumination luminosity is lowered when the luminosity of the acquired biometric data from the first image is higher than the predetermined luminosity.

4. The biometric authentication device according to claim 1,
 wherein the processor is further programmed by the executable instructions to:
 cause the visible light source to irradiate the finger inserting section only when authenticated by a first authentication operation executed before and different from the biometric authentication.

5. The biometric authentication device according to claim 1,
 wherein the processor is further programmed by the executable instructions to:
 cause the visible light source to change lighting patterns or lighting colors of the visible light depending on an authentication mode or a way the finger is placed as a result of the biometric authentication.

6. A biometric authentication method for carrying out biometric authentication using biometric information by collating pre-registered biometric data for authentication with biometric data acquired during authentication, the method comprising the steps of:
 irradiating visible light from a visible light source into a housing that defines a finger inserting section;
 irradiating a finger is disposed in the finger inserting section with near-infrared light from a near-infrared light source;
 capturing a first image of the finger in the finger inserting section with the near-infrared light which penetrates through the finger while the visible light source irradiates the finger inserting section with the visible light;
 acquiring biometric data from the first image; and
 when a luminosity of the acquired biometric data from the first image is higher than a predetermined luminosity, lowering an irradiation luminosity of the visible light, capturing a second image of the finger in the finger inserting section with the near-infrared light which penetrates through the finger while the visible light source irradiates the finger inserting section with the lowered visible light from the visible light source,
 acquiring biometric data from the second image, and
 collating the acquired biometric data from the second image with the pre-registered biometric data for authentication.

7. The biometric authentication method according to claim 6, further comprising:
 when the luminosity of the acquired biometric data from the first image is lower than the predetermined luminosity, maintaining the irradiation luminosity from the visible light source to be unchanged or lowering the irradiation luminosity from the visible light source,
 capturing a second image of the finger in the finger inserting section with the near-infrared light which penetrates through the finger while the visible light source irradiates the finger inserting section with the maintained or lowered visible light from the visible light source,
 acquiring biometric data from the second image, and
 collating the acquired biometric data from the second image with the pre-registered biometric data for authentication.

8. The biometric authentication method according to claim 7, wherein an amount the illumination luminosity is lowered when the luminosity of the acquired biometric data from the first image is higher than the predetermined luminosity is smaller than an amount the illumination luminosity is lowered when the luminosity of the acquired biometric data from the first image is higher than the predetermined luminosity.

* * * * *